United States Patent [19]

Mikkelsen

[11] Patent Number: Plant 5,877

[45] Date of Patent: Feb. 10, 1987

[54] KALANCHOE PLANT NAMED CHERRY JUBILEE

[75] Inventor: James C. Mikkelsen, Ashtabula, Ohio

[73] Assignee: Mikkelsens, Inc., Ashtabula, Ohio

[21] Appl. No.: 712,121

[22] Filed: Mar. 15, 1985

[51] Int. Cl.[4] ..... A01H 5/00

[52] U.S. Cl. ..... Plt/68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant name Cherry Jubilee, characterized by its cherry rose flower color, dense and symmetrical full growth, excellent basal and secondary branching, excellent keeping qualities, and by its pinkish white mature stigmas.

1 Drawing Figure

The present invention relates to a new and distinct cultivar of Kalanchoe plant, botanically known as *Kalanchoe blossfeldiana*, and known by the cultivar name Cherry Jubilee. Cherry Jubilee was developed by me through controlled breeding by crossing the unpatented cultivar Venus (seed parent) and Feuerball (pollen parent) Feuerball is disclosed in U.S. Plant Pat. No. 3,861.

Asexual reproduction by stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry:

1. Cherry Jubilee has better basal branching than either of its parents, as well as Royalty (disclosed in U.S. Plant Pat. No. 5,254) and Sensation (disclosed in U.S. Plant Pat. No. 4,727).

2. Cherry Jubilee is more compact in growth habit than Royalty, Sensation and Feuerball, and similar to Venus. Cherry Jubilee is highly suited for 10 cm pot production.

3. The color of Cherry Jubilee is a cherry rose, which is lighter in color than Venus with less blue pigment, and with less red pigment than Feuerball; intermediate in red pigment between Sensation and Royalty, with less than Royalty and more than Sensation.

4. Flower size is larger than Feuerball and similar to Royalty, Sensation, and Venus. Flower does not split calyx like Feuerball.

5. The number of flowers is more than Venus and equal to Feuerball, Sensation and Royalty; however, total effect is greater as flower clusters are not as open as Royalty, Sensation and Feuerball.

6. Mature stigmas are pinkish white while both parents have a white mature stigma, as does Royalty and Sensation.

7. Pedicels on the terminal flower cluster are shorter than on Feuerball, Venus, Sensation and Royalty.

8. Leaf is similar in size and shape to Venus, being rounded at the tip, while Royalty, Sensation and Feuerball all have a larger and more pointed leaf tip.

9. The plant is more symmetrical than either parent and has shorter internodes than Royalty and Sensation, thereby producing a dense full appearance.

10. After flower initiation, plants must be treated with B-9 in all seasons to reduce peduncle elongation.

11. Flowering time is 10 weeks in summer and 13 weeks in winter after start of short days, compared to Venus which is 10 weeks in summer and 14 weeks in winter; Royalty is 11 weeks in summer and 13 weeks in winter; Sensation is 11 weeks in summer and 14 weeks in winter; and, Feuerball is 10 weeks in summer and 14 weeks in winter, all as tested in Ashtabula, Ohio.

The accompanying colored photograph, taken in February of 1985, illustrates in perspective view the overall appearance of Cherry Jubilee, showing the colors as true as it is reasonably possible to obtain in a colored reproduction of this type.

The following is a detailed description of my new Kalanchoe cultivar grown in 10 cm plastic pots produced under commercial practices in the greenhouses of Mikkelsens Inc., Ashtabula, Ohio. Color references are made to The Horticultural Society Colour Chart except where general terms of ordinary dictionary significance are used.

Parentage: A controlled cross between Venus and Feuerball.

Propagation:

(A) *Type cutting.*—Short stem cutting up to 2 cm long.

(B) *Time to root.*—10 days at 21° C. summer, 14 days at 21° C. winter.

(C) *Rooting habit.*—Many fine fibrous roots.

Plant description:

(A) *Form.*—Compact, upright, well branched. Best suited for 10 cm pot growing and scheduling practices.

(B) *Habit of growth.*—Moderate rate of growth with branching from nearly every node.

(C) *Foliage.*—Leaves simple, opposite. (1) Size: Average full grown leaf of plant in flowering in a 10 cm pot is 120 mm long and 70 mm wide. (2) Shape: Ovate, apex obtuse, base attenuate. (3) Texture: Glabrous, coriaceous, succulent. (4) Margin: Crenate. (5) Color: young foliage, top side green 137C, under side green 137D. Mature foliage, top side yellow-green 147A, under side green 137C.

Flowering description:

(A) *Flowering habits.*—Cyme inflorescence; each shoot is formed by dichotomous branching, starting with the opening of the terminal flower of the main axis, followed by terminal flowers of the side branching, continuing with subsequent development of branches in the inflorescence. Major inflorescence is 100 to 110 mm in diameter and lateral inflorescences are 60 to 70 mm in diameter when grown in a 10 cm pot.

(B) *Natural flowering season.*—Mid-January. Flowering time under controlled daylength at 20° C. in summer is 10 weeks; in winter is 13 weeks. Flowering time depends on temperature, light intensity, and other growing conditions.

(C) *Flower buds.*—Oblong up to 7 mm long, developing to tubular as flower petals mature, sheathed with four green sepals; corolla at maturity 8 mm long.

(D) *Flowers borne.*—Compound dichasial cymes; peduncle 5 mm in diameter, with peduncle length depending on growing conditions and B-9 application; pedicels up to 10 mm long.

(E) *Quantity of flowers.*—Highly floriferous; main axis counted over 75 flowers and laterals over 50 flowers with 6 to 8 lateral branches.

(F) *Petals.*—(1) Shape: Nearly rounded, top cuspidate. (2) Color: Top side when opening, red 44B, fading to red-purple 58C; under side red 55B. (3) Number of petals: Four (4).

(G) *Reproductive organs.*—(1) Stamens: Eight (8) in number. (a) Anther shape: Flat, elliptical, color reddish yellow. (b) Filament color: Light green. (c) Pollen color: Yellow. (2) Pistels: (a) Stigma: Flat, immature color greenish yellow, mature color pinkish white. (b) Styles: Light green. (c) Ovaries: 4 celled, 6 mm in size, color light green.

Disease resistance: Highly resistant to Mildew. No other disease problems seen to date.

I claim:

1. A new and distinct cultivar of Kalanchoe plant named Cherry Jubilee, as illustrated and described, and particularly characterized by its cherry rose flower color, dense and symmetrical full growth, excellent basal and secondary branching, excellent keeping qualities, and by its pinkish white mature stigmas.

* * * * *

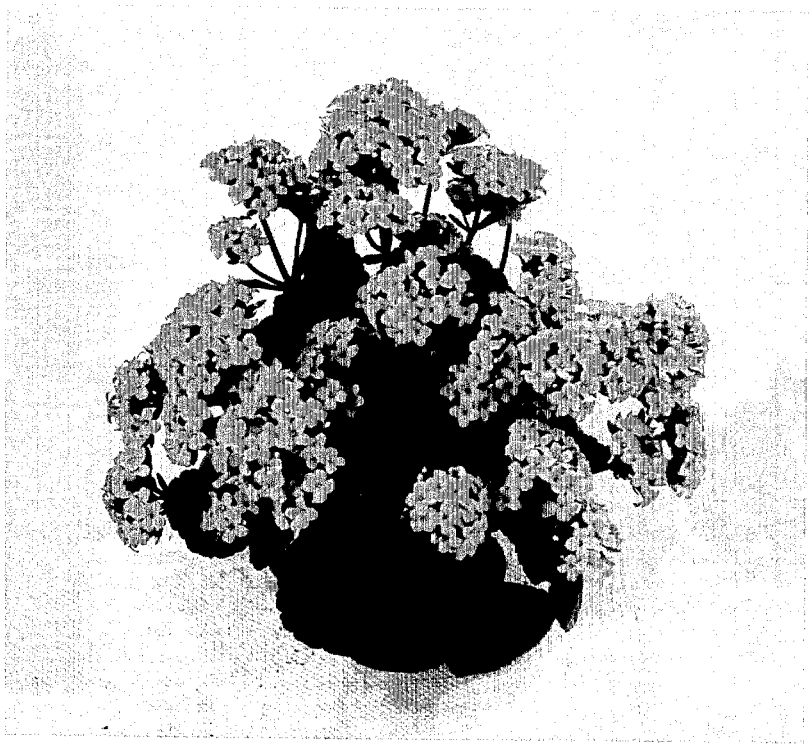

CHERRY JUBILEE